United States Patent
Bakhshinejad et al.

(10) Patent No.: US 11,600,379 B2
(45) Date of Patent: Mar. 7, 2023

(54) SYSTEMS AND METHODS FOR GENERATING CLASSIFYING AND QUANTITATIVE ANALYSIS REPORTS OF ANEURYSMS FROM MEDICAL IMAGE DATA

(71) Applicant: THE MEDICAL COLLEGE OF WISCONSIN, INC., Milwaukee, WI (US)

(72) Inventors: Ali Bakhshinejad, Milwaukee, WI (US); Kevin M. Koch, Wauwatosa, WI (US); Andrew S. Nencka, Franklin, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 128 days.

(21) Appl. No.: 16/931,069

(22) Filed: Jul. 16, 2020

(65) Prior Publication Data
US 2021/0020304 A1 Jan. 21, 2021

Related U.S. Application Data

(60) Provisional application No. 62/875,056, filed on Jul. 17, 2019.

(51) Int. Cl.
*G06K 9/00* (2022.01)
*G16H 30/40* (2018.01)
*G06T 7/143* (2017.01)
*G06N 20/00* (2019.01)
(Continued)

(52) U.S. Cl.
CPC .............. *G16H 30/40* (2018.01); *G06N 3/08* (2013.01); *G06N 20/00* (2019.01); *G06T 7/0014* (2013.01); *G06T 7/143* (2017.01); G06T 2207/20076 (2013.01); *G06T 2207/20081* (2013.01);
(Continued)

(58) Field of Classification Search
CPC .......... G16H 30/40; G06N 3/08; G06N 20/00; G06T 7/0014; G06T 7/143; G06T 2207/20076; G06T 2207/20081; G06T 2207/20084; G06T 2207/30101; G06T 2200/04; G06T 2207/10081; G06T 2207/10088; G06T 2207/10116; G06T 2207/30016; G06T 7/62; G06T 7/0016
See application file for complete search history.

(56) References Cited

U.S. PATENT DOCUMENTS

2012/0201446 A1* 8/2012 Yang ..................... G06T 7/0012
382/134

OTHER PUBLICATIONS

Chettrit, D., et al. "PHT-bot: a deep learning based system for automatic risk stratification of COPD patients based upon signs of pulmonary hypertension." Medical Imaging 2019: Computer-Aided Diagnosis. vol. 10950. International Society for Optics and Photonics, 2019.

(Continued)

*Primary Examiner* — Xin Jia
(74) *Attorney, Agent, or Firm* — Quarles & Brady LLP

(57) ABSTRACT

Aneurysms are classified and quantitatively analyzed based on medical image data acquired from a subject. In general, one or more algorithms are implemented to automatically classify, or otherwise diagnose, and measure aneurysms and their change over time. These algorithms make use of artificial intelligence and deep learning to develop quantitative analytics that can be consolidated into diagnostic reports.

46 Claims, 6 Drawing Sheets

(51) Int. Cl.
*G06N 3/08* (2023.01)
*G06T 7/00* (2017.01)
(52) U.S. Cl.
CPC .............. *G06T 2207/20084* (2013.01); *G06T 2207/30101* (2013.01)

(56) References Cited

OTHER PUBLICATIONS

Goldman. "Curvature Formulas for Implicit Curves and Surfaces," Computer Aided Geometric Design, 2005; 22:632-658.
Hong, H. A., et al. "Automatic detection, segmentation and classification of abdominal aortic aneurysm using deep learning." 2016 IEEE 12th International Colloquium on Signal Processing & Its Applications (CSPA). IEEE, 2016.
International Searching Authority. International Search Report and Written Opinion for application PCT/US2020/042335. dated Nov. 2, 2020. 16 pages.
Kakeda, S., et al. "Diagnostic accuracy and reading time to detect intracranial aneurysms on MR angiography using a computer-aided diagnosis system." American journal of roentgenology 190.2 (2008): 459-465.
López-Linares, K., et al. "Fully automatic detection and segmentation of abdominal aortic thrombus in post-operative CTA images using deep convolutional neural networks." Medical image analysis 46 (2018): 202-214.
Milletari, et al. "V-Net: Fully Convolutional Neural Networks for Volumetric Medical Image Segmentation," 2016 Fourth International Conference on 3D Vision (3DV), Stanford, CA, 2016, pp. 565-571.
Park, A., et al. "Deep learning-assisted diagnosis of cerebral aneurysms using the HeadXNet model." JAMA network open 2.6 (2019): e195600-e195600.
Ueda, D., et al. "Deep learning for MR angiography: automated detection of cerebral aneurysms." Radiology 290.1 (2019): 187-194.
Yang, X., et al. "Computer-aided detection of intracranial aneurysms in MR angiography." Journal of digital imaging 24.1 (2011): 86-95.

* cited by examiner

SYSTEMS AND METHODS FOR GENERATING CLASSIFYING AND QUANTITATIVE ANALYSIS REPORTS OF ANEURYSMS FROM MEDICAL IMAGE DATA

CROSS-REFERENCE TO RELATED APPLICATIONS

This application claims the benefit of U.S. Provisional Patent Application Ser. No. 62/875,056, filed on Jul. 17, 2019, and entitled "SYSTEMS AND METHODS FOR GENERATING CLASSIFYING AND QUANTITATIVE ANALYSIS REPORTS OF ANEURYSMS FROM MEDICAL IMAGE DATA," which is herein incorporated by reference in its entirety.

BACKGROUND

An intracranial aneurysm ("ICA") is an abnormal dilation of an artery usually near arterial bifurcation in circle of Willis. The disease is the result of weakening of the intima layer of the blood vessel which results in ballooning of the lumen into an abnormal shape. The incremental improvement in the resolution of cerebral medical imaging techniques such as MRI and CT in the recent years resulted in more incidental findings of this type of disease which some believe is as high as 7%. Due to poor results in treatment of the ICA rupture (i.e. subarachnoid hemorrhage (SAH)) which are 40% fatal, there is a pressing need for clinicians to be provided with a more accurate method evaluating the current stage and future development of the disease. Currently, the clinician needs to choose between treatment and observation based on available risk factors such as: age, gender, location and size of the disease, and other family history of SAH or similar aneurysms. However, the current methods of dilation measurements can be variable from a radiologist to another.

SUMMARY OF THE DISCLOSURE

The present disclosure addresses the aforementioned drawbacks by providing a method for generating a report that classifies and quantitatively analyzes one or more aneurysms in a subject. The method includes accessing medical image data with a computer system, wherein the medical image data depict vasculature in a subject; generating a binary vasculature mask by segmenting the medical image data using the computer system, wherein the binary vasculature mask has first binary values indicating a presence of vasculature at a voxel location and second binary values indicating an absence of vasculature at a voxel location; generating classified feature data with the computer system by inputting the binary vasculature mask to a trained machine learning algorithm, generating output as the classified feature data, wherein the classified feature data classify regions in the vasculature of the subject as being associated with an aneurysm; generating a probability map from the classified feature data using the computer system, wherein the probability map indicates a probability of locations in the vasculature of the subject being associated with an aneurysm; computing quantitative parameters with the computer system by fitting a basis set of geometrical objects to values in the probability map, wherein the quantitative parameters quantify aneurysm geometry; and generating a report from the quantitative parameters using the computer system, wherein the report indicate a quantitative analysis of one or more aneurysms in the vasculature of the subject.

It is another aspect of the present disclosure to provide A method for constructing and implementing a machine learning algorithm to generate a binary vasculature mask whose values indicate a presence or absence of vasculature in a subject. The method includes constructing a trained machine learning algorithm and generating a binary vasculature mask by inputting medical image data acquired from a subject to the trained machine learning algorithm. The trained machine learning algorithm is constructed by accessing training data with a computer system, the training data comprising medical image data acquired from a plurality of subjects and labeled data indicating a locations in the medical image data corresponding to vasculature in each of the plurality of subjects; and training a machine learning algorithm based on the training data, wherein the machine learning algorithm is trained on the training data to generate a binary vasculature mask whose values indicate a presence or absence of vasculature at locations in a subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for classifying and quantitatively analyzing aneurysms based on medical image data acquired from a subject. In general, the systems and methods implement one or more algorithms to automatically classify, or otherwise diagnose, and measure aneurysms and their change over time. These algorithms make use of artificial intelligence and deep learning to develop quantitative analytics that can be consolidated into diagnostic reports.

As one example, deep learning through deep residual neural networks ("ResNet") can be used to generate a report that indicates classification and quantitative analysis of an aneurysm. Briefly, such networks apply the concept utilized by mammalian visual systems and so-called skip connectors (also known as shortcuts) to effectively train the system, including the weights and biases of all the available neurons, to perform an image-based task.

In one aspect of the systems and methods described in the present disclosure, medical image data are input to a suitably trained machine learning algorithm, such as a ResNet, generating output as a binary classification map (aneurysm detection map, which may be referred to as a binary vasculature mask or map), which locates and measures abnormalities in the vasculature. Using this map, descriptive geometric parameters can be derived and summarized in a report. Parameters can include regional size of aneurysm(s) and confidence interval(s) within highlighted regions (indicating clarity of aneurysm in a CTA/MRI image).

In some embodiments, the algorithms described in the present disclosure take medical image data (e.g., upwards of thousands or tens of thousands of MRI images, CT images, or both) and training images as input and passes them through a deep neural network model to generate as output a radiological characteristic diagnostic report and a three-dimensional rendering of the abnormal neurovascular region.

Figure 1:
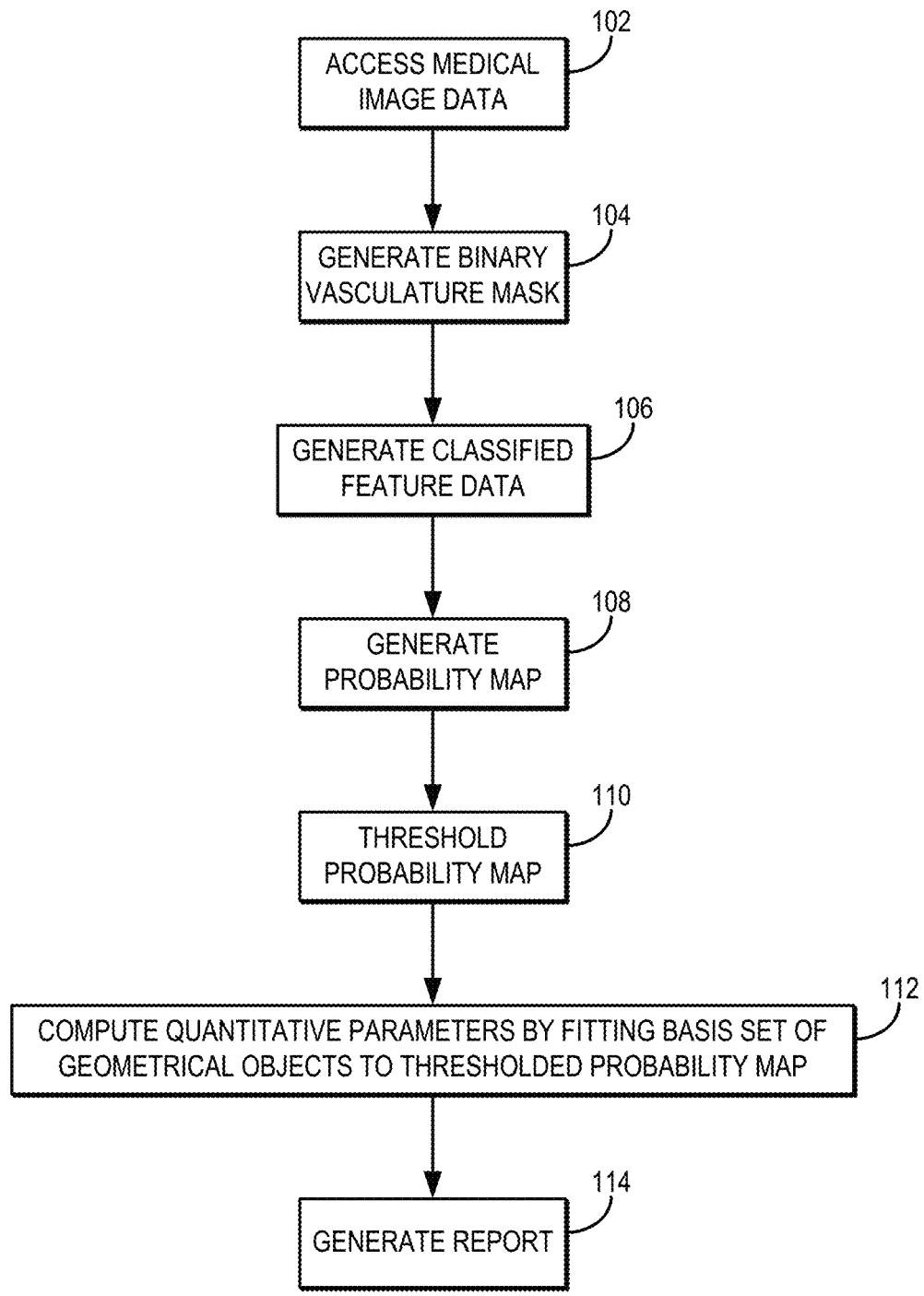
FIG. 1 is a flowchart setting forth the steps of an example method for generating a report that classifies and indicates a quantitative analysis of aneurysms based on medical image data.

Referring now to FIG. 1, a flowchart is illustrated as setting forth the steps of an example method for generating a report that classifies and indicates a quantitative analysis of aneurysms based on medical image data. The method includes accessing medical image data with a computer system, as indicated at step 102. Accessing the medical image data can include retrieving medical image data from a memory or other data storage device or medium. The medical image data may also be accessed by acquiring medical image data with a suitable medical imaging system and communicating the acquired medical image data to the computer system, which may be a part of the medical imaging system.

In general, the medical image data may include magnetic resonance images; x-ray images, such as those acquired with an x-ray computed tomography ("CT") system or a C-arm system; or other suitable medical images that depict the vasculature in a subject, such as the cerebrovasculature. In some instances, the medical image data may include data acquired with a medical imaging system (e.g., k-space data acquired with an MRI system). In these instances, medical images can be reconstructed from the data using the computer system.

A binary vasculature mask is generated from the medical image data, as indicated at step 104. The binary vasculature mask, which may be referred to as a "vascular cast," contains voxels (which may also be pixels) whose binary values indicate the presence of a vascular structure within that voxel. For instance, voxels in the binary vasculature mask can have values of "1" to indicate the presence of vasculature within that voxel and values of "0" to indicate the absence of vasculature within that voxel. That is, the binary vasculature mask classifies voxels as either a vasculature location ("1") or non-vasculature location ("0").

In general, the binary vasculature mask can be generated by segmenting the medical image data. In some embodiments, the binary vasculature mask can be generating by segmenting the medical image data using image segmentation techniques, such as region growing. In other embodiments, the binary vasculature mask can be generated by inputting the medical image data to a trained machine learning algorithm that has been trained to segment vasculature from non-vasculature locations in medical image data.

As one non-limiting example, a residual neural network ("ResNet") can be implemented to generate the binary vasculature mask. A ResNet is advantageous because it is able to ease the training of very deep networks compared to standard convolutional neural networks. In some instances, the ResNet can be constructed by stacking several residual blocks. Shortcut, or "skip," connections are used to take the activation from one layer and feed it to another layer. In this way, a very deep network can be trained with significantly reduced training errors that may otherwise be present when training very deep standard networks. As one example, convolutional layers with a very small receptive field (e.g., 3×3) can be utilized. The number of feature maps increases as the number of residual blocks increases, doubling after each block. The output is a binary classification map (aneurysm detection map or binary vasculature mask), which locates and measures abnormalities in the vasculature. It will be appreciated that other suitable neural networks can also be trained and implemented to segment vasculature for generating the binary vasculature mask. For instance, a V-Net, such as the one described by F. Milletari, et al., in "V-Net: Fully Convolutional Neural Networks for Volumetric Medical Image Segmentation," 2016 Fourth International Conference on 3D Vision (3DV), Stanford, Calif., 2016, pp. 565-571, can also be implemented.

Classified feature data are then generated using the binary vasculature mask, as indicated at step 106. The classified feature data may include a feature map whose voxels (which may also be pixels) are classified as being associated with an aneurysm, such as an intracranial aneurysm ("ICA"). For instance, the classified feature data can be generated by inputting the binary vascular mask to a trained machine learning algorithm that has been trained to classify aneurysms, generating output as the classified feature data.

As one example, the trained machine learning algorithm can be a neural network-based classifier. In some implementations, the neural network may be a deep neural network. Additionally or alternatively, the neural network may be a patch-wise neural network. For instance, the trained machine learning algorithm may be a two-dimensional or three-dimensional convolutional neural network. For instance, a neural network with a ResNet-based architecture can be trained and implemented as a deep CNN classifier. Aneurysm classification results from such a network can include, among others, bounding boxes around identified aneurysms.

Using the classified feature data, a probability map is generated, as indicated at step 108. This probability map indicates the probability of a voxel being associated with an aneurysm. The probability map can be generated, for example, using classified patch volumes contained in the classified feature data. In some instances, previously generated classified feature data may be accessed with the computer system, and the probability map can be generated from that previously generated classified feature data. The probability map is then thresholded to identify regions for which quantitative metrics describing aneurysms are to be generated, as indicated at step 110. As one example, voxels with a probability greater than 0.5 can be selected. As another example, voxels with a probability greater than 0.7 can be selected. Other threshold values can also be used, depending on the desired tolerances.

Quantitative parameters are then computed by fitting the identified or otherwise selected voxels to a basis set of geometrical objects, as indicated at step 112. In some instances, the classified feature data may include selected voxels that can be input to this fitting process. For instance, the classified feature data may include one or more bounding boxes that define regions of voxels that are identified as being associated with an aneurysm. For example, a 3D volume, defined by such a bounding box, can be extracted from the binary vascular mask. This region of interest contains the full aneurysm sac, as well as a segment of the parent vessel. Thus, in some instances, the steps of generating and thresholding a probability map do not need to be performed.

The basis set of geometrical objects may include a basis set of ellipsoids, cylinders, toroids, or other suitable geometrical object or shape. As one example, the voxels (e.g., the binary vasculature mask voxels identified or selected as having the threshold probability of belonging to an aneurysm) can be fit to the basis set of geometrical objects based on a one-dimensional fitting. The quantitative parameters can include parameters of these geometrical objects, such as volume (e.g., integrated volume), orientation, and dimensions (e.g., major and minor axis of ellipsoids, height and radius of cylinders). These parameters can be used to measure and report the size and location of the aneurysm. Advantageously, these quantitative parameters can be tracked over time to provide an objective measure of changes in an identified aneurysm. This process removes a level of subjectivity otherwise seen in conventional clinical approaches for monitoring aneurysms. In some instances, a previously generated probability map can be accessed with the computer system, and the quantitative parameters can be computed by fitting voxels in that probability map to a basis set of geometrical objects.

In one non-limiting example, aneurysm surfaces identified or otherwise determined from the selected voxels can be fit with a basis set of geometrical objects that includes radial basis functions ("RBFs"). These interpolating functions, fit to the acquired image data, can model aneurysms with a super-resolution manifold. As described below, differential geometry or other suitable quantitative analyses, may then be applied to these manifolds to quantitatively characterize aneurysms.

Fitting the selected voxels to RBFs has particular advantages for characterizing aneurysms. As one advantage, RBFs interpolate the aneurysm surface with arbitrary resolution, enabling a super-resolution modeling of the aneurysm. Interpolators enable higher resolution representations of continuous surfaces that are sampled at a lower resolution. High resolution surfaces that vary smoothly can be well-approximated from very low resolution data. Because the surfaces of aneurysms are smooth at diagnostically-relevant length scales, radial basis functions can be used to estimate aneurysm surfaces at higher resolutions than are obtainable with clinical magnetic resonance angiographic techniques.

As another advantage, the RBFs are mathematically smooth, which enables the use of differential geometry to quantify surface curvature. Because the RBFs are mathematically smooth, they have defined derivatives at all points. Based on this property, characteristics of the surface curvature are well defined, and can be analytically computed at all locations on the surface. This characterization of the curvature of the aneurysm surface can be used for the algorithmic detection and measurement of aneurysms.

As still another advantage, RBFs yield a continuous manifold, which can ensure that any ray originating from its internal surface will intersect the surface at another point, thereby enabling robust aneurysm size quantification. Manifolds are continuous, without any holes, and can locally be analyzed using Euclidean geometric methods. These properties, which are not guaranteed with other methods (such as mesh surface rendering with the marching cubes algorithm), are favorable for surface modeling. In example implementations, the guaranteed lack of holes can be utilized when performing quantitative aneurysm measurements.

In general, RBFs are mathematical models that are dependent upon both the radial distance of a point from the center of its basis function and the location of the center of the basis function. An implicit surface can be defined through the linear combination of a set of these basis functions with varying center locations.

As one non-limiting example, a radial basis function can be defined using the following multiquadratic function:

$$\phi_0(\vec{r}_a) = \sqrt{1+(\varepsilon(\vec{r}_a - \vec{r}_0))^2} \qquad (1);$$

where $\vec{r}_a$ is the measured point of the function, $\vec{r}_0$ is the center location, and $\varepsilon$ is an arbitrary scale factor. A full surface, $s(\vec{r}_a)$, can be approximated by the manifold wherein the sum of N different radial basis functions is equal to zero, $$s(\vec{r}_a) = \sum_{i=0}^{N} w_i \phi_0(\vec{r}_a) = 0; \qquad (2)$$

where $w_i$ is a real-valued, multiplicative weighting factor for the ith basis function, which has a unique center location. The weighting factors may be solved through a simple system of linear equations evaluated at given points on the surface and defined by a set of N basis functions.

In some instances, based on the fitting of the selected voxels to the RBFS (or other basis set of geometrical objects), a high-resolution vascular cast can be generated, from which the quantitative parameters can then be computed. For example, a high-resolution vascular cast can be generated by using the fit RBF models and evaluating the functions on a grid of points with higher resolution than the observed data. As noted above, RBFs yield an "implicit surface," meaning that the modeled surface can be defined at points in space where the radial basis function decomposition yields a value of zero. Following an evaluation of the basis functions on a high-resolution grid, the zero surface can be extracted as the interpolated aneurysm cast. This cast can be a fully closed surface, with the aneurysm surface and feeding vessel defined.

As one non-limiting example, the quantitative parameters can include the curvature of the vessel and aneurysm casts. Aneurysms can manifest with complex geometrical forms. The curvature of these forms can be characterized by taking spatial derivatives of the aneurysm surface structure. With RBFs, these spatial derivatives are well-defined through the principles of differential geometry. For instance, the cumulative derivative of a surface can be defined through the sum of the derivatives of the individual RBFs, $$\frac{\partial}{\partial r}(s(\vec{r})) = \sum_{i=0}^{N} \frac{w_i \varepsilon^2 (\vec{r} - \vec{r}_i)}{\sqrt{\varepsilon^2 (\vec{r} - \vec{r}_i)^2 + 1}}; \qquad (3)$$

and the gradient requires only partial derivatives along orthogonal spatial dimensions. Similarly, the second derivative, or Hessian, which includes information regarding surface curvature, can be defined through further partial differentiation. While these functions are described in spherical coordinates for simplicity, in practice a transform of coordinates to the Cartesian system can also be used, as it may be more appropriate for imaging data reconstructed on a Cartesian grid.

With the gradient and Hessian computed, the Gaussian curvature of the modeled surface can be computed, as are the principal curvatures. Details of these relationships are derived for implicit surfaces by R. Goldman in "Curvature Formulas for Implicit Curves and Surfaces," *Computer Aided Geometric Design,* 2005; 22:632-658. Again, through the use of RBFs, these metrics can be analytically computed at each location on the surface with arbitrary resolution, avoiding computationally intensive and imprecise discrete numerical methods.

As another example, the computed quantitative parameters can include rays normal to the internal surface of the aneurysm (again analytically computed with differential geometry), which can be generated utilizing the RBF-interpolated surface. The lengths of line segments arising from those rays, which intersect the opposite edge of the modeled aneurysm manifold, are computed. This can yield an analytic map of aneurysm dimensions, defined at all points on the aneurysm surface.

Referring still to FIG. 1, a report can then be generated by the computer system, as indicated at step 114. The report may include a data structure storing quantitative parameters, images, data plots, textual information, and combinations thereof. For instance, the report may include a data structure that contains quantitative parameters related to one or more identified aneurysms, which may be displayed alongside or otherwise together with images from the medical image data. In some implementations, a three-dimensional ("3D") rendering of the abnormal neurovascular region, or regions, can be generated from the medical image data and provided as a part of the report. The report may this be generated and stored for later use, or may be displayed to a user. As one example, the report may be generated by the computer system and displayed to a user via a graphical user interface, which may enable user interaction with the report, such as by manipulating views of the 3D rendering, selecting different images from the medical image data for display, presenting quantitative parameters, and so on.

When the computed quantitative parameters include the curvature of the vessel and/or aneurysm cast, the generating the report may include identifying and reporting the location of the aneurysm neck based on the spatial distribution of such a curvature map. All aneurysms include an intersection of the aneurysm sac with the parent vessel. This neck generally corresponds with a region of saddle geometry on the surface of the aneurysm. Meanwhile, the sac of the aneurysm can be well modeled as one or more intersecting convex structures. In this way, curvature (e.g., Gaussian curvature) can be well-suited to identify these regions of the aneurysm. For example, regions where the curvature (e.g., Gaussian curvature) is greater than zero correspond to regions in which the aneurysm surface is convex, like the sac. Conversely, regions where the curvature (e.g., Gaussian curvature) is less than zero correspond to regions in which the aneurysm surface is saddle shaped, like the neck. The largest region of negative curvature can be identified as laying on the neck of the aneurysm.

When the computed quantitative parameters include line segments normal to the surface of the aneurysm, generating the report can include extracting and reporting metrics from the array of these spanning line segments. The distribution of spanning line segment lengths extending from the aneurysm neck (which may be identified by thresholding the Gaussian curvature surface as described above) can be analyzed to develop a reduced set of geometric metrics. For each point of maximal curvature on the aneurysm neck, several segments originating along the first principal curve for the point can be extracted for analysis. Segments spanning the neck of the aneurysm can be identified as the minimum of a valley in the sequence of spanning line segments as longer segments on either side intersect the sac of the aneurysm and the parent vessel wall.

Similarly, the height of the aneurysm sac can be computed using normal line segments. In these instances, the distribution of normal line segments that intersect the neck spanning line segments is compiled. The aneurysm sac height can then be selected as the maximum of this population.

As described above, numerous other metrics of aneurysm shape, curvature, and volume can be extracted through the modeling procedures described in the present disclosure. These metrics can be compiled and these aneurysm-specific engineered features can be used for radiomic analysis or other analysis techniques.

Figure 2:
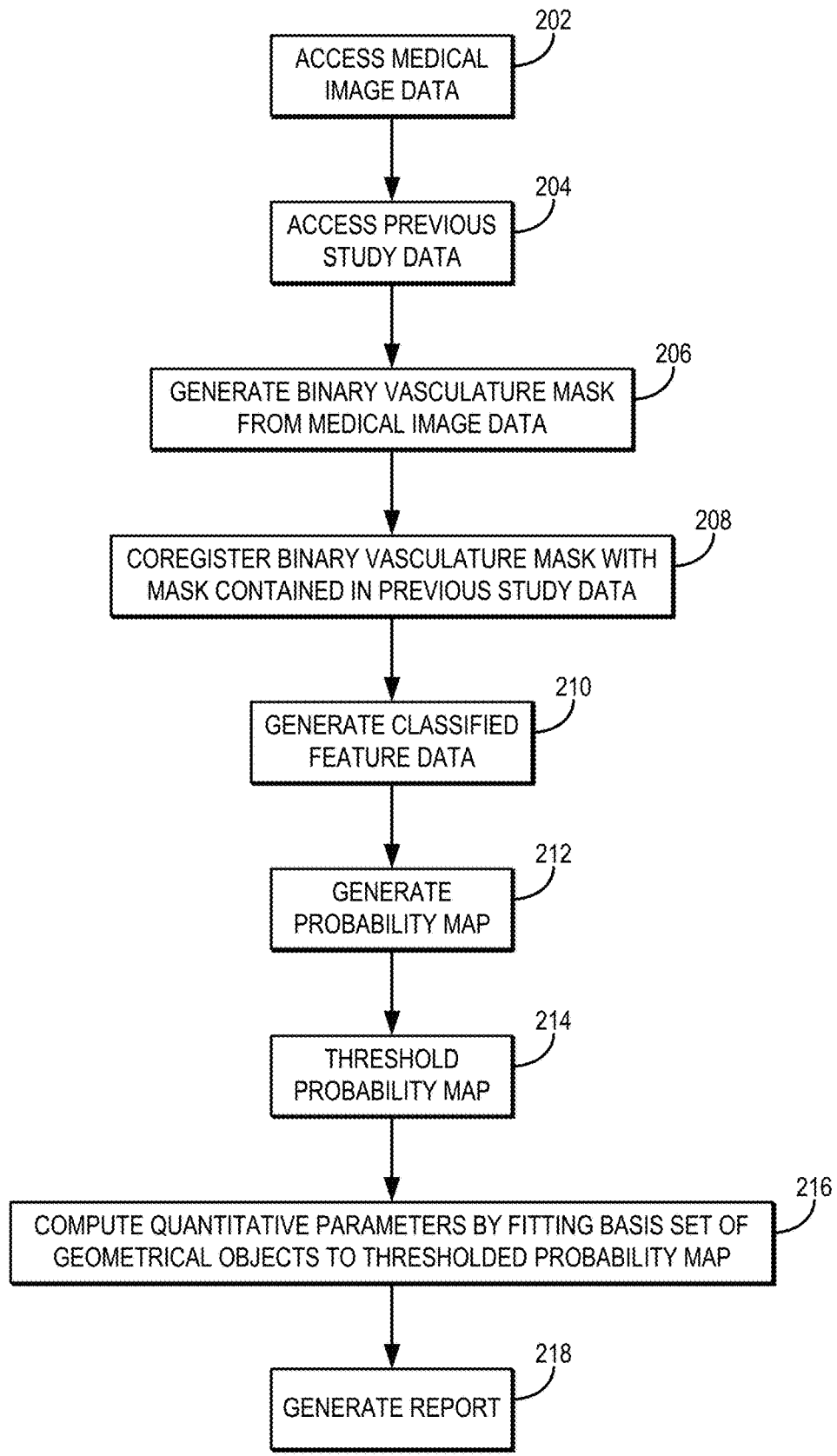
FIG. 2 is a flowchart setting forth the steps of an example method for tracking changes in an aneurysm over time using classification and analysis reports generated in accordance with embodiments described in the present disclosure.

Referring now to FIG. 2, a flowchart is illustrated as setting forth the steps of an example method for tracking changes in an aneurysm over time using classification and analysis reports generated in accordance with embodiments described in the present disclosure. The method includes accessing medical image data with a computer system, as indicated at step 202. Similar to the methods described above, accessing the medical image data can include retrieving medical image data from a memory or other data storage device or medium. The medical image data may also be accessed by acquiring medical image data with a suitable medical imaging system and communicating the acquired medical image data to the computer system, which may be a part of the medical imaging system. As above, the medical image data may include magnetic resonance images; x-ray images, such as those acquired with an x-ray computed tomography ("CT") system or a C-arm system; or other suitable medical images that depict the vasculature in a subject, such as the cerebrovasculature.

Previous study data are also accessed with the computer system, as indicated at step 204. These previous study data include a binary vasculature mask generated from an earlier time point, in addition to quantitative parameters computed based on that binary vasculature mask. Additionally, the previous study data may also include medical image data and a classification and analysis report.

A binary vasculature mask is generated from the medical image data, as indicated at step 206. In general, the binary vasculature mask can be generated by segmenting the medical image data. In some embodiments, the binary vasculature mask can be generating by segmenting the medical image data using image segmentation techniques, such as region growing. In other embodiments, the binary vasculature mask can be generated by inputting the medical image data to a trained machine learning algorithm that has been trained to segment vasculature from non-vasculature locations in medical image data. The current mask is then co-registered with the previous mask, as indicated at step 208. As one example, an iterative closest algorithm can be used to register the two masks, which when registered can be used as a baseline to measure the changes of the aneurysm over time.

Classified feature data are then generated using the co-registered binary vasculature mask, as indicated at step 210.

The classified feature data may include a feature map whose voxels (which may also be pixels) are classified as being associated with an aneurysm, such as an ICA. For instance, the classified feature data can be generated by inputting the binary vascular mask to a trained machine learning algorithm that has been trained to classify aneurysms, generating output as the classified feature data.

Using the classified feature data, a probability map is generated, as indicated at step 212. This probability map indicates the probability of a voxel being associated with an aneurysm. The probability map can be generated, for example, using classified patch volumes contained in the classified feature data. The probability map is then thresholded to identify regions for which quantitative metrics describing aneurysms are to be generated, as indicated at step 214. As one example, voxels with a probability greater than 0.5 can be selected. As another example, voxels with a probability greater than 0.7 can be selected. Other threshold values can also be used, depending on the desired tolerances.

Quantitative parameters are then computed by fitting the identified or otherwise selected voxels to a basis set of geometrical objects, as indicated at step 216. As above, the basis set of geometrical objects may include a basis set of ellipsoids, cylinders, toroids, or other suitable geometrical object or shape. As one example, the voxels (e.g., the binary vasculature mask voxels identified or selected as having the threshold probability of belonging to an aneurysm) can be fit to the basis set of geometrical objects based on a one-dimensional fitting. The quantitative parameters can include parameters of these geometrical objects, such as volume (e.g., integrated volume), orientation, and dimensions (e.g., major and minor axis of ellipsoids, height and radius of cylinders). These parameters can be used to measure and report the size and location of the aneurysm.

Preferably, the same basis set of geometric objects is used to compute the quantitative parameters in the current study as was used in the previous study data. In this way, the quantitative parameters can be more directly compared. Similarly, by co-registering the current binary vasculature mask with the binary vasculature mask contained in the previous study data, direction comparisons can be made with the previously acquired and generated data. As such, the comparisons provide an objective measure of changes in an identified aneurysm over time. This process removes a level of subjectivity otherwise seen in conventional clinical approaches for monitoring aneurysms.

A report can then be generated by the computer system, as indicated at step 218. The report may include a data structure storing quantitative parameters, images, data plots, textual information, and combinations thereof. For instance, the report may include a data structure that contains quantitative parameters related to one or more identified aneurysms, which may be displayed alongside or otherwise together with images from the medical image data. As an example, the report may indicate the size, geometry, or other characteristics or properties of the aneurysm. For instance, the report may include quantitative parameters such as the integrated volume of geometrical objects to which the voxels were fit and/or the major and minor axes when the geometrical objects are ellipsoids. Still other quantitative parameters, such as those described above, can be used and reported. These quantitative parameters can be reported as numerical or textual information, and in some instances can be reported on a user interface, such as a graphical user interface. The quantitative parameters can also be reported alongside images of the subject, display elements that depict the geometrical objects, or both. For example, display elements that depict the geometrical objects can be generated and overlaid with the images of the subject, and the quantitative parameters associated with those geometrical objects can be reported alongside the display elements and the images. As one example, the quantitative parameters can be displayed to a user based on an interaction with one of the display elements that depicts the corresponding geometrical object (e.g., a user clicking on the display element that represents that geometrical object).

The report may also contain information indicating a change in the aneurysm relative to the previous study data. For instance, the report may include numerical indications, textual indications, visual indications, or combinations thereof, that represent changes in the aneurysm over time. As an example, the report may indicate a change in the size, geometry, or other characteristics or properties of the aneurysm.

In some implementations, a three-dimensional ("3D") rendering of the abnormal neurovascular region, or regions, can be generated from the medical image data and provided as a part of the report. The report may this be generated and stored for later use, or may be displayed to a user. As one example, the report may be generated by the computer system and displayed to a user via a graphical user interface, which may enable user interaction with the report, such as by manipulating views of the 3D rendering, selecting different images from the medical image data for display, presenting quantitative parameters, and so on.

Thus, the systems and methods described in the present disclosure provide for an automation of the otherwise time-consuming diagnosis process for aneurysms, while increasing accuracy by highlighting the regions-of-interest. This workflow provides more structured data to the radiologist to assist the radiologist at achieving a more accurate diagnosis. Using the systems and methods described in the present disclosure, the productivity and efficiency of a radiologist can be significantly increased, such as by an order of magnitude. Additionally, the systems and methods described in the present disclosure are unique in that they provide disease measurements as a standard radiology report that goes beyond a simple binary diagnostic.

Figure 3:
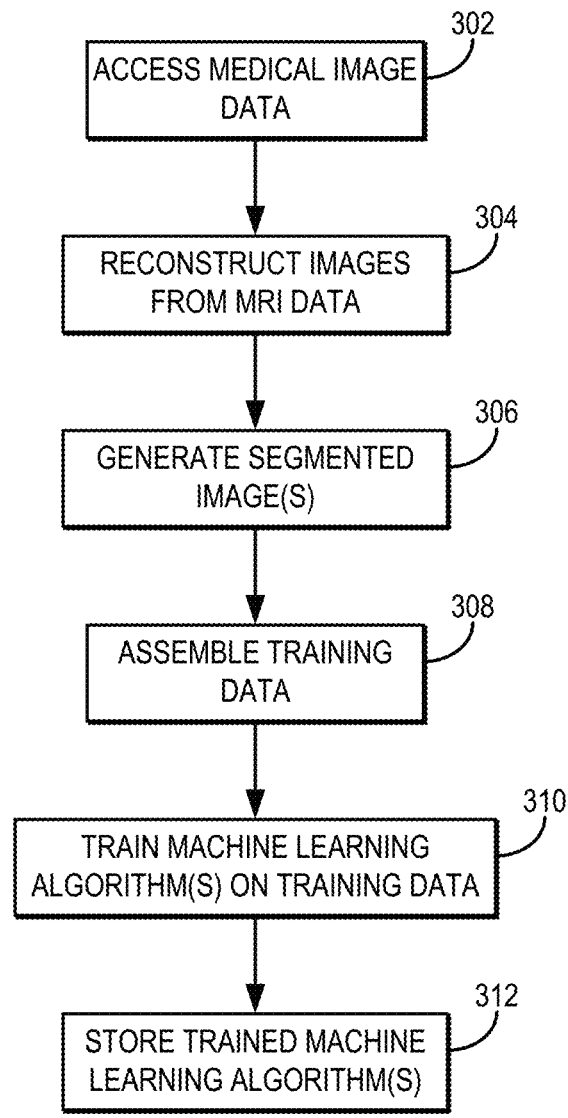
FIG. 3 is a flowchart setting forth the steps of an example method for training one or more machine learning algorithms on training data, such that the one or more machine learning algorithms are trained to receive input as medical image data in order to generate output as one or more binary vasculature masks.
Figures 4A, 4B:
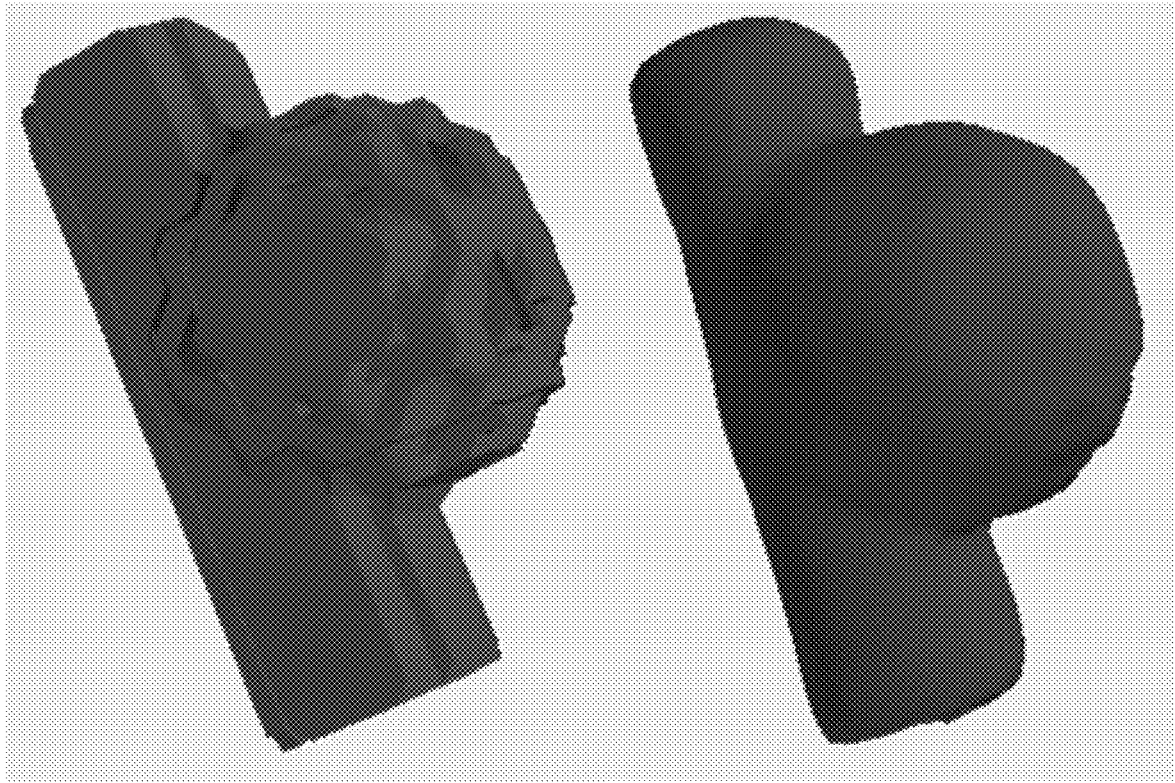
FIGS. 4A-4D show an example of modeling and quantifying an aneurysm according to some embodiments described in the present disclosure.
Figures 4C, 4D:

Referring now to FIG. 3, a flowchart is illustrated as setting forth the steps of an example method for training one or more machine learning algorithms on training data, such that the one or more machine learning algorithms are trained to receive input as medical image data in order to generate output as one or more binary vasculature masks. The method includes accessing medical image data with a computer system, as indicated at step 302. Accessing the medical image data can include retrieving medical image data from a memory or other data storage device or medium. The medical image data may also be accessed by acquiring medical image data with a suitable medical imaging system and communicating the acquired medical image data to the computer system, which may be a part of the medical imaging system.

In general, the medical image data may include magnetic resonance images; x-ray images, such as those acquired with an x-ray computed tomography ("CT") system or a C-arm system; or other suitable medical images that depict the vasculature in a subject, such as the cerebrovasculature. In some instances, the medical image data may include data acquired with a medical imaging system (e.g., k-space data acquired with an MRI system). In these instances, medical images can be reconstructed from the data using the computer system.

Cloned data are generated from the medical image data, as indicated at step 304. As an example, the cloned data can be generated by making copies of the medical image data in which alterations or modifications have been made to the original medical image data. For instance, cloned data can be generated using data augmentation techniques, such as adding noise to the original medical image data, performing a deformable transformation (e.g., translation, rotation, both) on the original medical image data, smoothing the original medical image data, applying a random geometric perturbation to the original medical image data, combinations thereof, and so on. The cloned data can be generated based on a cloning ratio. For instance, a cloning ratio of 1:5,000 may be used, in which 5,000 cloned data are generated for each input medical image data. Other cloning ratios can also be implemented. The cloned data can be generated based on a single input medical image contained in the medical image data, or based on more images. As another non-limiting example, the medical image data may contain as few as five medical images and the cloned data can be generated from those five images.

Segmented data are then generated at step 306 by segmenting the medical image data and the cloned data. The segmented data can be generated by manually, semi-automatically, or automatically segmenting images.

Training data are assembled next, as indicated at step 308. Assembling the training data may include assembling medical image data, cloned data, segmented data, and other relevant data. For instance, assembling the training data may include generating labeled data and including the labeled data in the training data. Labeled data may include medical image data, cloned data, segmented data, or other relevant data that have been labeled as belonging to, or otherwise being associated with, one or more different classifications or categories. For instance, labeled data may include medical image data, cloned data, and/or segmented data that have been labeled based on a probability of a locations being associated with vasculature. The labeled data may include labeling all data within a field-of-view of the medical image data, cloned data, and/or the segmented data, or may include labeling only those data in one or more ROIs in the medical image data, cloned data, and/or the segmented data. The labeled data may include data that are classified on a voxel-by-voxel basis, or a regional or larger volume basis.

One or more machine learning algorithms are trained on the training data, as indicated at step 310. The machine learning algorithm can be any suitable machine learning algorithm, and in some instances includes a machine learning algorithm based on a neural network. The neural network may be a convolutional neural network, and in some instances may include a residual neural network.

The one or more trained machine learning algorithms are then stored for later use, as indicated at step 312. Storing the machine learning algorithms may include storing weights, biases, or both, which have been computed or otherwise estimated by training the machine learning algorithm on the training data. When the machine learning algorithm implements a neural network, storing the trained machine learning algorithm may include storing the particular neural network architecture to be implemented. For instance, data pertaining to the layers in the neural network architecture (e.g., number of layers, type of layers, ordering of layers, connections between layers) may be stored.

As shown in FIGS. 4A-4D, an example of aneurysm modeling with RBFs according to some of the methods described in the present disclosure includes interpolating the acquired resolution aneurysm cast (FIG. 4A) to a higher resolution (FIG. 4B) using a fit RBF model. Analytic measurements of Gaussian curvature (FIG. 4C) are computed at each point on the aneurysm surface using differential geometry applied to the RBF model, and the neck of the aneurysm is identified with the negative Gaussian curvature. The lengths of aneurysm spanning line segments (FIG. 4D) are also guaranteed to exist because the RBF models a manifold, and are calculated as part of the fitting process. Segments used for identifying neck width are noted with an arrow.

Figure 5:
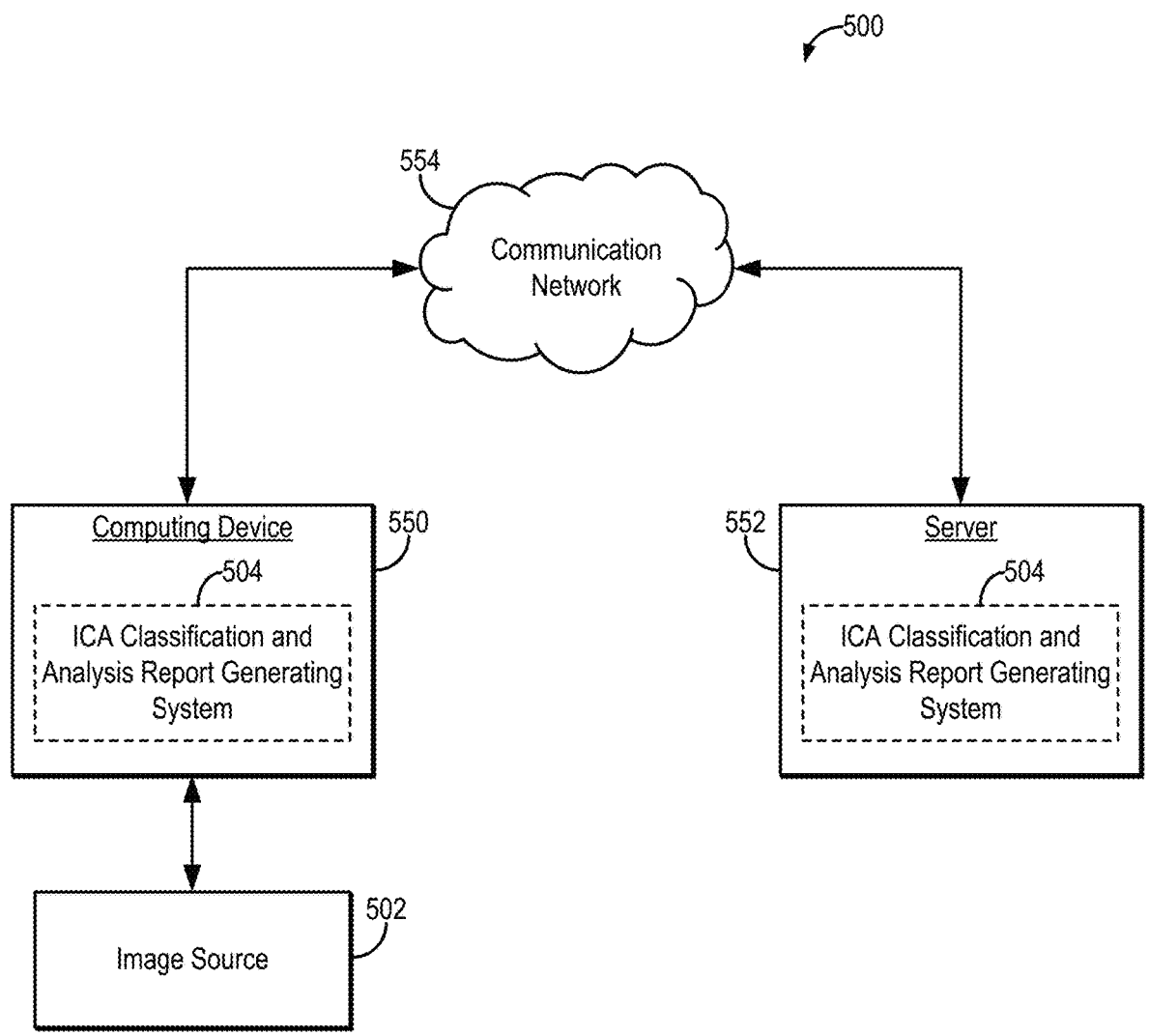
FIG. 5 is a block diagram of an example system for generating a classification and quantitative analysis report of an aneurysm from medical image data.

Referring now to FIG. 5, an example of a system 500 for classifying and analyzing aneurysms, such as intracranial aneurysms ("ICA"), in accordance with some embodiments of the systems and methods described in the present disclosure is shown. As shown in FIG. 5, a computing device 550 can receive one or more types of data (e.g., medical image data, training data) from image source 502, which may be a medical image source. In some embodiments, computing device 550 can execute at least a portion of an ICA classification and analysis report generating system 504 to generate a report that classifies and indicates quantitative analysis of aneurysms from data received from the image source 502.

Additionally or alternatively, in some embodiments, the computing device 550 can communicate information about data received from the image source 502 to a server 552 over a communication network 554, which can execute at least a portion of the ICA classification and analysis report generating system 504 to generate a report that classifies and indicates quantitative analysis of aneurysms from data received from the image source 502. In such embodiments, the server 552 can return information to the computing device 550 (and/or any other suitable computing device) indicative of an output of the ICA classification and analysis report generating system 504.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, image source 502 can be any suitable source of image data (e.g., measurement data, images reconstructed from measurement data), such as a medical imaging system (e.g., an MRI system, a CT system, and x-ray C-arm system), another computing device (e.g., a server storing image data), and so on. In some embodiments, image source 502 can be local to computing device 550. For example, image source 502 can be incorporated with computing device 550 (e.g., computing device 550 can be configured as part of a device for capturing, scanning, and/or storing images). As another example, image source 502 can be connected to computing device 550 by a cable, a direct wireless link, and so on. Additionally or alternatively, in some embodiments, image source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 554 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
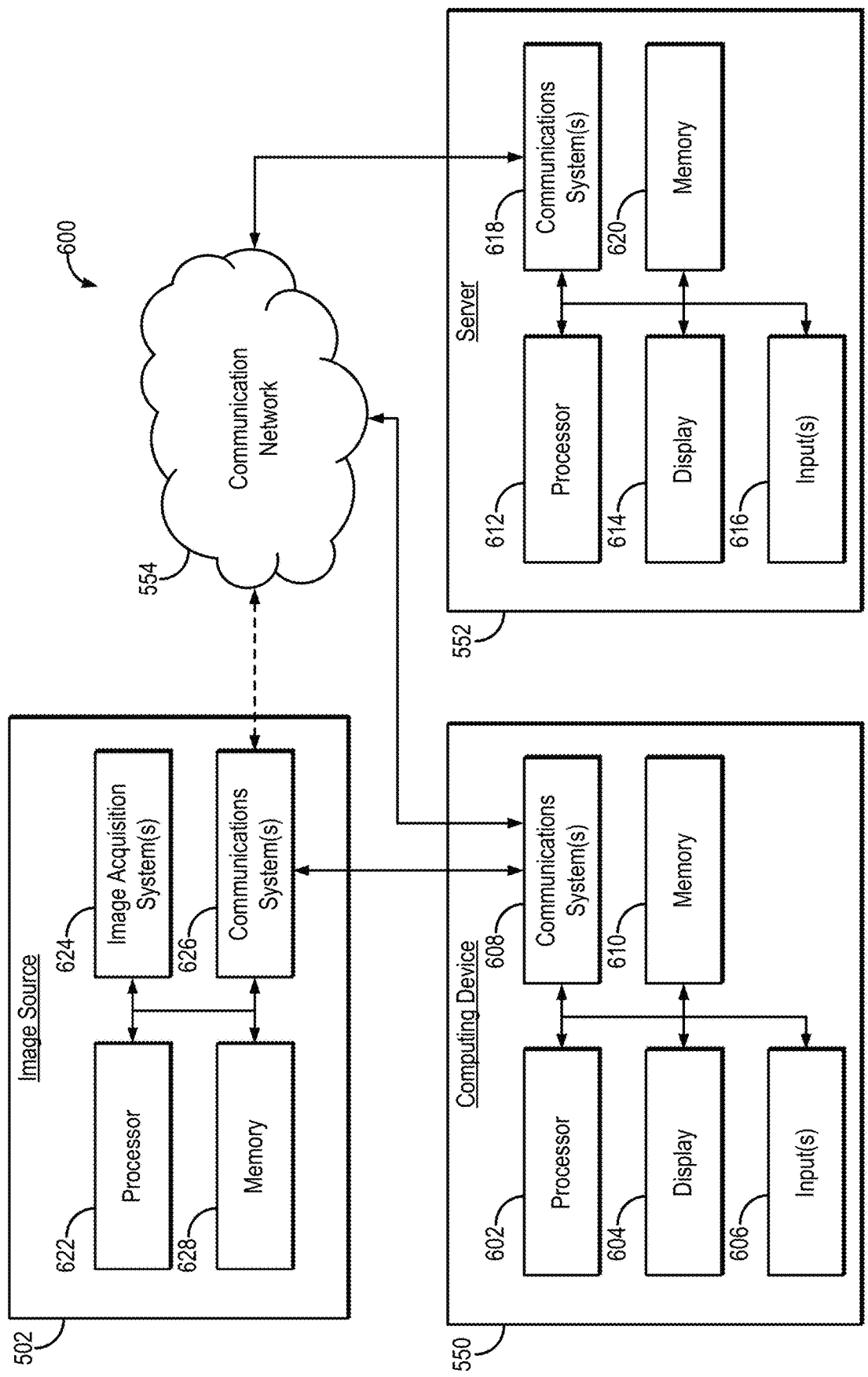
FIG. 6 is a block diagram of example components that can implement the system of FIG. 5.

Referring now to FIG. 6, an example of hardware 600 that can be used to implement image source 502, computing device 550, and server 552 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, image source 502 can include a processor 622, one or more image acquisition systems 624, one or more communications systems 626, and/or memory 628. In some embodiments, processor 622 can be any suitable hardware processor or combination of processors, such as a CPU, a GPU, and so on. In some embodiments, the one or more image acquisition systems 624 are generally configured to acquire data, images, or both, and can include a medical imaging system (e.g., an MRI system, a CT system, an x-ray C-arm system). Additionally or alternatively, in some embodiments, one or more image acquisition systems 624 can include any suitable hardware, firmware, and/or software for coupling to and/or controlling operations of a medical imaging system. In some embodiments, one or more portions of the one or more image acquisition systems 624 can be removable and/or replaceable.

Note that, although not shown, image source 502 can include any suitable inputs and/or outputs. For example, image source 502 can include input devices and/or sensors that can be used to receive user input, such as a keyboard, a mouse, a touchscreen, a microphone, a trackpad, a trackball, and so on. As another example, image source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more image acquisition systems 624, and/or receive data from the one or more image acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of image source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a report that classifies and quantitatively analyzes one or more aneurysms in a subject, the method comprising:
   (a) accessing medical image data with a computer system, wherein the medical image data depict vasculature in a subject;
   (b) generating a binary vasculature mask by segmenting the medical image data using the computer system, wherein the binary vasculature mask has first binary values indicating a presence of vasculature at a voxel location and second binary values indicating an absence of vasculature at a voxel location;
   (c) generating classified feature data with the computer system by inputting the binary vasculature mask to a trained machine learning algorithm, generating output as the classified feature data, wherein the classified feature data classify regions in the vasculature of the subject as being associated with an aneurysm;
   (d) computing quantitative parameters with the computer system by fitting a basis set of geometrical objects to values in the classified feature data, wherein the quantitative parameters quantify aneurysm geometry; and
   (e) generating a report from the quantitative parameters using the computer system, wherein the report indicates a quantitative analysis of one or more aneurysms in the vasculature of the subject.

2. The method as recited in claim 1, wherein the binary vasculature mask is generating by inputting the medical image data to a second trained machine learning algorithm that is trained on training data to segment vasculature from medical image data, generating output as the binary vasculature mask.

3. The method as recited in claim 2, wherein the second trained machine learning algorithm implements a neural network.

4. The method as recited in claim 3, wherein the neural network is a residual neural network.

5. The method as recited in claim 1, wherein the classified feature data comprise a probability map computed using the computer system, wherein the probability map indicates a probability of locations in the vasculature of the subject being associated with an aneurysm; and
   wherein computing the quantitative parameters with the computer system comprises fitting the basis set of geometrical objects to values in the probability map.

6. The method as recited in claim 5, wherein the probability map is thresholded using a threshold value to identify locations in the probability map that are associated with an aneurysm, and wherein the quantitative parameters are computed by fitting the basis set of geometrical objects to the values in the identified locations in the probability map.

7. The method as recited in claim 1, wherein the basis set of geometrical objects comprises ellipsoids.

8. The method as recited in claim 7, wherein the quantitative parameters comprise at least one of a major axis of an ellipsoid, a minor axis of an ellipsoid, a volume of an ellipsoid, and an orientation of an ellipsoid.

9. The method as recited in claim 1, wherein the basis set of geometrical objects comprises cylinders.

10. The method as recited in claim 9, wherein the quantitative parameters comprise at least one of a height of a cylinder, a radius of a cylinder, a volume of a cylinder, and an orientation of a cylinder.

11. The method as recited in claim 1, wherein the basis set of geometrical objects comprises at least one of ellipsoids, cylinders, toroids, spheres, and combinations thereof.

12. The method as recited in claim 1, wherein the basis set of geometrical objects comprises radial basis functions.

13. The method as recited in claim 12, wherein the quantitative parameters comprise a curvature computed based on fitting the radial basis functions to the classified feature data.

14. The method as recited in claim 13, wherein the curvature is a Gaussian curvature.

15. The method as recited in claim 13, wherein the report indicates a location of a neck of the one or more aneurysms.

16. The method as recited in claim 12, wherein the quantitative parameters comprise one or more line segments normal to a surface defined based on fitting the radial basis functions to the classified feature data.

17. The method as recited in claim 12, wherein computing the quantitative parameters with the computer system comprises generating a high-resolution vascular cast by fitting the radial basis functions to values in the classified feature data and computing the quantitative parameters from the high-resolution vascular cast;
wherein the high-resolution vascular cast has higher spatial resolution than the medical image data.

18. The method as recited in claim 17, wherein the high-resolution vascular cast is generated by evaluating models generated by fitting the radial basis functions to the values in the classified feature data on a grid of points the with higher spatial resolution than the medical image data.

19. The method as recited in claim 1, wherein the report is generated also using the medical image data, such that the report includes a visual depiction of the vasculature in the subject.

20. The method as recited in claim 1, wherein the report is generated also using the binary vasculature mask, such that the report includes a visual depiction of segmented vasculature in the subject.

21. The method as recited in claim 1, further comprising:
accessing previous study data from the subject, wherein the previous study data comprise a previous binary vasculature mask of the subject;
co-registering the binary vasculature mask with the previous binary vasculature mask before inputting the binary vasculature mask to the trained machine learning algorithm; and
wherein the report indicates a change in quantitative parameters relative to the previous study data, thereby indicating a change in the one or more aneurysms in the subject over time.

22. The method as recited in claim 1, wherein the trained machine learning algorithm implements a neural network.

23. The method as recited in claim 22, wherein the neural network is a residual neural network.

24. The method as recited in claim 1, wherein the medical image data comprises images acquired with at least one of a magnetic resonance imaging system, a computed tomography system, and an x-ray C-arm system.

25. The method as recited in claim 1, wherein the classified feature data comprise a bounding box identifying a region of voxels in the binary vasculature map associated with an aneurysm.

26. A method for generating a report that classifies and quantitatively analyzes one or more aneurysms in a subject, the method comprising:
(a) accessing a probability map with a computer system, wherein the probability map indicates a probability of locations in a vasculature of a subject being associated with an aneurysm;
(b) computing quantitative parameters with the computer system by fitting a basis set of geometrical objects to values in the probability map, wherein the quantitative parameters quantify aneurysm geometry;
(c) generating a report from the quantitative parameters using the computer system, wherein the report indicates a quantitative analysis of one or more aneurysms in the vasculature of the subject;
further comprising;
accessing a binary vasculature mask of the subject with the computer system, wherein the binary vasculature mask has first binary values indicating a presence of vasculature at a voxel location and second binary values indicating an absence of vasculature at a voxel location; and
wherein the report is generated also using the binary vasculature mask, such that the report includes a visual depiction of segmented vasculature in the subject.

27. The method as recited in claim 26, wherein the basis set of geometrical objects comprises ellipsoids.

28. The method as recited in claim 27, wherein the quantitative parameters comprise at least one of a major axis of an ellipsoid, a minor axis of an ellipsoid, a volume of an ellipsoid, and an orientation of an ellipsoid.

29. The method as recited in claim 26, wherein the basis set of geometrical objects comprises cylinders.

30. The method as recited in claim 29, wherein the quantitative parameters comprise at least one of a height of a cylinder, a radius of a cylinder, a volume of a cylinder, and an orientation of a cylinder.

31. The method as recited in claim 26, wherein the basis set of geometrical objects comprises radial basis functions.

32. The method as recited in claim 31, wherein the quantitative parameters comprise a curvature computed based on fitting the radial basis functions to the classified feature data.

33. The method as recited in claim 31, wherein the quantitative parameters comprise one or more line segments normal to a surface defined based on fitting the radial basis functions to the classified feature data.

34. The method as recited in claim 26, wherein the basis set of geometrical parameters comprises at least one of ellipsoids, cylinders, toroids, spheres, and combinations thereof.

35. The method as recited in claim 26, further comprising:
accessing medical image data of the subject with the computer system; and
wherein the report is generated also using the medical image data, such that the report includes a visual depiction of the vasculature in the subject.

36. The method as recited in claim 26, further comprising thresholding the probability map using a threshold value to identify regions in the probability map most probable to be associated with an aneurysm, and wherein the quantitative parameters are computed by fitting the basis set of geometrical objects to values in identified regions in the probability map.

37. A method for generating a report that classifies and quantitatively analyzes one or more aneurysms in a subject, the method comprising:
(a) accessing a probability map with a computer system, wherein the probability map indicates a probability of locations in a vasculature of a subject being associated with an aneurysm;
(b) computing quantitative parameters with the computer system by fitting a basis set of geometrical objects to values in the probability map, wherein the quantitative parameters quantify aneurysm geometry;
(c) generating a report from the quantitative parameters using the computer system, wherein the report indicates a quantitative analysis of one or more aneurysms in the vasculature of the subject; and
further comprising thresholding the probability map using a threshold value to identify regions in the probability map most probable to be associated with an aneurysm, and wherein the quantitative parameters are computed by fitting the basis set of geometrical objects to values in identified regions in the probability map.

38. The method as recited in claim 37, wherein the basis set of geometrical objects comprises ellipsoids.

39. The method as recited in claim 38, wherein the quantitative parameters comprise at least one of a major axis of an ellipsoid, a minor axis of an ellipsoid, a volume of an ellipsoid, and an orientation of an ellipsoid.

40. The method as recited in claim 37, wherein the basis set of geometrical objects comprises cylinders.

41. The method as recited in claim 40, wherein the quantitative parameters comprise at least one of a height of a cylinder, a radius of a cylinder, a volume of a cylinder, and an orientation of a cylinder.

42. The method as recited in claim 37, wherein the basis set of geometrical objects comprises radial basis functions.

43. The method as recited in claim 42, wherein the quantitative parameters comprise a curvature computed based on fitting the radial basis functions to the classified feature data.

44. The method as recited in claim 42, wherein the quantitative parameters comprise one or more line segments normal to a surface defined based on fitting the radial basis functions to the classified feature data.

45. The method as recited in claim 37, wherein the basis set of geometrical parameters comprises at least one of ellipsoids, cylinders, toroids, spheres, and combinations thereof.

46. The method as recited in claim 37, further comprising:
   accessing medical image data of the subject with the computer system; and
   wherein the report is generated also using the medical image data, such that the report includes a visual depiction of the vasculature in the subject.

* * * * *